(12) United States Patent
Xie et al.

(10) Patent No.: US 10,746,656 B2
(45) Date of Patent: Aug. 18, 2020

(54) $CO_2$ QUANTITATIVE FLUORESCENT SENSING MATERIAL, PREPARATION METHOD AND APPLICATION THEREOF

(71) Applicant: Yancheng Institute of Technology, Yancheng (CN)

(72) Inventors: Minghua Xie, Yancheng (CN); Xiuli Yang, Yancheng (CN); Rong Shao, Yancheng (CN); Guihua Hou, Yancheng (CN); Rongfeng Guan, Yancheng (CN)

(73) Assignee: Yancheng Institute of Technology, Yancheng (CN)

( * ) Notice: Subject to any disclaimer, the term of this patent is extended or adjusted under 35 U.S.C. 154(b) by 327 days.

(21) Appl. No.: 15/834,140

(22) Filed: Dec. 7, 2017

(65) Prior Publication Data

US 2018/0284023 A1  Oct. 4, 2018

(30) Foreign Application Priority Data

Mar. 28, 2017  (CN) .......................... 2017 1 0192479

(51) Int. Cl.
*G01N 21/64*  (2006.01)
*G01N 33/00*  (2006.01)
(Continued)

(52) U.S. Cl.
CPC ......... *G01N 21/6428* (2013.01); *G01N 21/11* (2013.01); *G01N 33/004* (2013.01);
(Continued)

(58) Field of Classification Search
CPC .. G01N 33/004; G01N 21/11; G01N 21/7786; G01N 21/64; G01N 21/6407; G01N 21/6428
See application file for complete search history.

(56) References Cited

U.S. PATENT DOCUMENTS

2011/0015086 A1* 1/2011 Sun ...................... C12Q 1/6837
   506/9
2013/0011912 A1* 1/2013 Battrell ................ G01N 21/645
   435/287.2
(Continued)

FOREIGN PATENT DOCUMENTS

CN  102721681 A  10/2012
CN  104059632 A  9/2014
(Continued)

OTHER PUBLICATIONS

Fan Shunli, et al., Highly Sensitive Determination of Carbon Dioxide with H2O2-Luminol-Uranine-K2CO3 Chemiluminescent Reaction, Acta Chimic Sinica, 2006, 64 (18):1876-1880.

*Primary Examiner* — David P Porta
*Assistant Examiner* — Djura Malevic
(74) *Attorney, Agent, or Firm* — Wayne & Ken, LLC; Tony Hom

(57) ABSTRACT

The present disclosure discloses a $CO_2$ quantitative fluorescent sensing material, a preparation method and an application thereof. The preparation method for the $CO_2$ quantitative fluorescent sensing material includes dissolving 9,10-diacrylic anthracene in a solvent to prepare 5-10 mg/mL of a first solution; dissolving $MnCl_2$ or $Mn(ClO_4)_2$ in water to prepare 50-100 mg/mL of a second solution; mixing the first solution and the second solution; adding a diluted acid into the mixed solution; sealing and heating the mixed solution. This preparation method is simple. During application, an ionic liquid produced by a reaction of $CO_2$ gas and an amine compound improves an aggregation-induced emission of the $CO_2$ quantitative fluorescent sensing material and a fluorescence thereof is significantly improved. So that a fluorescent $CO_2$ quantification is performed rapidly and accurately.

9 Claims, 4 Drawing Sheets

(51) Int. Cl.
*G01N 21/11* (2006.01)
*G01N 21/77* (2006.01)
*G01N 31/22* (2006.01)

(52) U.S. Cl.
CPC ... *G01N 31/223* (2013.01); *G01N 2021/6432* (2013.01); *G01N 2021/6439* (2013.01); *G01N 2021/7786* (2013.01); *Y02A 50/244* (2018.01)

(56) References Cited

U.S. PATENT DOCUMENTS

2016/0265030 A1\* 9/2016 Tsukuda ................ C12Q 1/686
2017/0045484 A1\* 2/2017 Han ..................... G01N 33/004

FOREIGN PATENT DOCUMENTS

| | | |
|---|---|---|
| CN | 104926885 A | 9/2015 |
| CN | 104927835 A | 9/2015 |
| CN | 105566331 A | 5/2016 |
| CN | 105820813 A | 8/2016 |
| WO | 2012045046 A2 | 4/2012 |

\* cited by examiner

CO₂ QUANTITATIVE FLUORESCENT SENSING MATERIAL, PREPARATION METHOD AND APPLICATION THEREOF

TECHNICAL FIELD

The present disclosure relates to a field of $CO_2$ detection technology, and specifically to a $CO_2$ quantitative fluorescent sensing material, a preparation method and an application thereof.

BACKGROUND

The widespread use of fossil fuels and related industrial emissions have led to an increase in air $CO_2$ emission year by year and the greenhouse effect caused by $CO_2$ has obviously started to affect a normal living environment of all mankind. Therefore, it is of great significance to detect a concentration of $CO_2$ in the air rapidly and accurately for improving the living environment. In addition, accurate detection of $CO_2$ concentrations is also of great value to many industries. For example, detecting a $CO_2$ concentration in greenhouses can effectively increase a crop yield in agricultural production; detecting a $CO_2$ concentrations can help reduce respiratory disease and improve people's health level in a health system; detecting a $CO_2$ concentration in volcanic gas can effectively predict a volcanic eruption cycle; detecting a $CO_2$ emission from production equipment can indirectly monitor an operation of equipment and improve a production efficiency. In all, a rapid and accurate detection of a $CO_2$ concentration is extremely important for the survival of all walks of life and even for the human beings.

$CO_2$ is a colorless, odorless and chemically inert gas, so accurate detection of its concentration is rather difficult. Current detection technologies of $CO_2$ concentration include acid-base titration, gas chromatography, electrochemical and infrared spectroscopy. Wherein the acid-base titration method is extremely cumbersome, and the accuracy is unsatisfactory. So there is almost little application value. Although an accuracy of a result can be obtained by the gas chromatography, a large equipment is required, and sampling steps are complex and difficult to apply to an on-spot detection rapidly. The electrochemical method mainly detects $CO_2$ relying on a change in potential, current or resistance brought by a reaction of $CO_2$ with electrodes. However, this method is slow in speed and easily interfered with by other acid gases or water, and the application is greatly restricted. Infrared spectroscopy is currently the most widely used technique for $CO_2$ detection. It takes advantage of a characteristic absorption of $CO_2$ carbonyl groups and calculates a concentration of $CO_2$ according to the Lambertil's law. It has great advantages such as fast analysis, non-pollution and portability, but it has fatal disadvantages. Since CO has a very similar infrared absorption to $CO_2$, and in some cases it is hard to avoid a generation of CO, an interference caused by CO cannot be eliminated in the infrared spectroscopy, greatly affecting an accuracy of detection. In addition, infrared spectroscopy and electrochemical methods are very sensitive to a moisture content, further limiting their applications. In all, there is an urgent need to develop a new $CO_2$ detection method that can detect a $CO_2$ concentration rapidly and accurately without an interference of CO and water for production, living and scientific researches.

SUMMARY

A purpose of the present disclosure is to provide a $CO_2$ quantitative fluorescent sensing material which detects a concentration of $CO_2$ rapidly and accurately without any interference.

Another purpose of the present disclosure is to provide a preparation method of the $CO_2$ quantitative fluorescent sensing material with a simple operation.

Another purpose of the present disclosure is to provide an application of the $CO_2$ quantitative fluorescent sensing material. The ionic liquid produced by a reaction of the $CO_2$ with an amine compound improves an aggregation-induced emission of the $CO_2$ quantitative fluorescent sensing material and a fluorescence thereof is significantly improved. So that a fluorescent $CO_2$ quantification is performed rapidly and accurately.

Technical solutions to solve the technical problem of the present disclosure are as follows.

The present invention provides a preparation method of a $CO_2$ quantitative fluorescent sensing material which comprises:

dissolving 9,10-diacrylic anthracene in a solvent and obtaining a first solution of 5-10 mg/mL;

the solvent is any one of N,N-dimethylformamide, N,N-dimethylacetamide and N, N-diethylformamide;

dissolving $MnCl_2$ or $Mn(ClO_4)_2$ in water and obtaining a second solution of 50-100 mg/mL;

mixing the first solution and the second solution in a volume ratio of 4:1.-1:4;

adding a diluted acid with a $H^+$ concentration of 0.3-1 mol/L and obtaining a mixed solution; and sealing and heating the mixed solution for 2-6 days under a heating temperature at 70-90° C.

Further, the diluted acid is a diluted nitric acid or a diluted hydrochloric acid.

Further, the mixed solution is sealed and heated in a glass spawn bottle.

The present invention also provides a $CO_2$ quantitative fluorescent sensing material, which is prepared by the method mentioned above.

A fluorescent $CO_2$ quantification is performed using the $CO_2$ quantitative fluorescent sensing material as a fluorescent detection material.

Further, a specific method for the fluorescent $CO_2$ quantification using the $CO_2$ quantitative fluorescent sensing material comprises:

obtaining standard fluorescence emission spectra by measuring an amine dispersion of the $CO_2$ quantitative fluorescent sensing material after an introduction of mixed gases of $CO_2$ and N2 containing various concentrations of $CO_2$ respectively to the amine dispersion;

marking a concentration of $CO_2$ as x, and marking corresponding fluorescent intensity of a maximum emission peak of the standard fluorescent spectra as y;

graphing a standard curve with a linear relationship by at least 10 groups of x, y values;

obtaining the linear relationship between the concentrations of $CO_2$ and the fluorescent intensity of the maximum emission peak of the standard fluorescence emission spectra of the $CO_2$ quantitative fluorescent sensing material with the mixed gases containing various concentrations of $CO_2$;

recording a fluorescence emission spectrum of the amine dispersion of the $CO_2$ quantitative fluorescent sensing material after introduction of a mixed gas containing an unknown concentration of $CO_2$, and marking a maximum emission peak as y'; and calculating a concentration of $CO_2$ to be x' in the gas to be tested according to the linear relationship.

Further, in a preferred embodiment of the present disclosure, a method for obtaining the standard fluorescence emission spectrum of the amine dispersion of the $CO_2$ quantitative fluorescent sensing material after each introduction of the mixed gases of $CO_2$ and $N_2$ containing various concentrations of $CO_2$ to the amine dispersion comprises:

weighing 1 mg of the $CO_2$ quantitative fluorescent sensing material and adding the $CO_2$ quantitative fluorescent sensing material into a quartz cuvette;

adding 1 mL of an amine compound into the quartz cuvette, and introducing 20-30 mL of the mixed gas of $CO_2$ and $N_2$ containing a certain concentration of $CO_2$;

sealing die quartz cuvette immediately after introducing the mixed gas, and obtaining a reference dispersion;

recording the fluorescence emission of the reference dispersion in a wavelength range of 425-700 nm; and obtaining the standard fluorescence emission spectrum corresponding to the certain concentration of $CO_2$.

Further, a method for measuring the fluorescence emission spectrum of the amine dispersion of the $CO_2$ quantitative fluorescent sensing material for the gas to be tested containing an unknown concentration of $CO_2$ comprises:

weighing 1 mg of the $CO_2$ quantitative fluorescent sensing material, and adding the $CO_2$ quantitative fluorescent sensing material into a quartz cuvette;

adding 1 mL of the amine compound, then introducing the gas to be tested containing the unknown concentration of $CO_2$ with a amount of the mixed gas same to the corresponding standard fluorescence spectrum test;

controlling a flow rate of the gas to be tested containing the unknown concentration of $CO_2$ with a flow rate of the mixed gas same to the corresponding standard fluorescence spectrum test;

sealing the quartz cuvette immediately after introducing the gas to be tested containing the unknown concentration of $CO_2$, and obtaining a dispersion to be tested;

recording, the fluorescence emission of the dispersion of the $CO_2$ quantitative fluorescent sensing material in a wavelength range of 425-700 nm; and obtaining a fluorescence emission spectrum.

Further, a fluorescence spectrophotometer is used for recording the fluorescence emission spectrum; and an excitation wavelength is set to be 402 nm before use.

Further, the amine compound is di-n-propylamine, di-n-butylamine di-n-hexylamine, propylamine, diethylamine, diisopropylamine, n-butylamine, diisobutylamine, N-methylpiperazine, or N,N dimethylethylenediamine.

Beneficial effects of the fluorescent sensing material for $CO_2$ quantification, preparation and application thereof in the present disclosure is as follows.

The preparation method of the $CO_2$ quantitative fluorescent sensing material of an embodiment in the present disclosure includes: dissolving 9,10-diacrylic anthracene in a solvent and obtaining a first solution of 5-10 mg/mL; the solvent is any one of N,N-dimethylformamide, N, N-dimethylacetamide and N,N-diethylformamide; dissolving $MnCl_2$ or $Mn(ClO_4)_2$ in water and obtaining a second solution of 50-100 mg/mL; mixing the first solution and the second solution in a proportion of 4:1-1:4; adding a diluted acid with a $H^+$ concentration of 0.3-1 mol/L and obtaining a mixed solution; sealing and heating the mixed solution for 2-6 days under a heating temperature at 70-90° C. This method is simple and the prepared $CO_2$ quantitative fluorescent sensing material can detect a $CO_2$ concentration rapidly and accurately without any interference. During application, the ionic liquid produced by reaction of the $CO_2$ with an amine compound improves an aggregation-induced emission of the $CO_2$ quantitative fluorescent sensing material and a fluorescence thereof is significantly improved. So that a fluorescent $CO_2$ quantification is performed rapidly and accurately,

BRIEF DESCRIPTION OF DRAWINGS

In order to describe clearly the technical solutions of embodiments of the present disclosure, a brief introduction of drawings is given to describe the embodiments. It is to, be understood that the following drawings merely illustrate some embodiments of the present disclosure and therefore, should not be regarded as a limitation of a scope of the present disclosure. For those skilled in the art, other related drawings may also be obtained based on the drawings mentioned above without any creative work.

DETAILED DESCRIPTION

In order to make objectives of embodiments, technical solutions, and advantages of the present disclosure clearly, the technical solutions in the embodiments or the present disclosure are described below. In the embodiments, if specific conditions are not mentioned, embodiments are performed according to normal conditions or conditions suggested by a manufacturer. Reagents or instruments used which are not specified in manufacturers, are all available conventional products through a commercial purchase.

The fluorescent sensing material for $CO_2$ quantification, the preparation method and the application thereof in the embodiments of the present disclosure are described in detail below.

The present disclosure provides the preparation method of the fluorescent sensing material for $CO_2$ quantification, wherein it includes the following steps.

Step 1: 910-diacrylic anthracene is dissolved in a solvent to obtain a last solution of 5-10 mg/mL. The solvent is any one of N,N-dimethylformamide, N,N-dimethylacetamide, N, N-diethylformamide, $MnCl_2$ or $Mn(ClO_4)_2$ is dissolved in water to obtain a second solution of 50-100 mg/mL.

Step 2: the first solution and the second solution are mixed m a proportion of 4:1-1:4. Then a diluted acid is added with a $H^+$ concentration of 0.3-1 mol/L into the mixed solution. The diluted acid is preferably a nitric acid or a hydrochloric acid. An adding amount is about 3-7 drops and a mixed solution is obtained.

Step 3: the mixed solution is sealed and heated for 2-6 days, preferably in a glass spawn bottle. A heating temperature is 70-90° C. A target product of the $CO_2$ quantitative fluorescent sensing material named ADA-Mn is obtained, and is generally an orange needle crystal.

The embodiments of the present disclosure also provides a $CO_2$ quantitative fluorescent sensing material named ADA-Mn which is prepared by the preparation method of the $CO_2$ quantitative fluorescent sensing material mentioned above.

Figure 1:
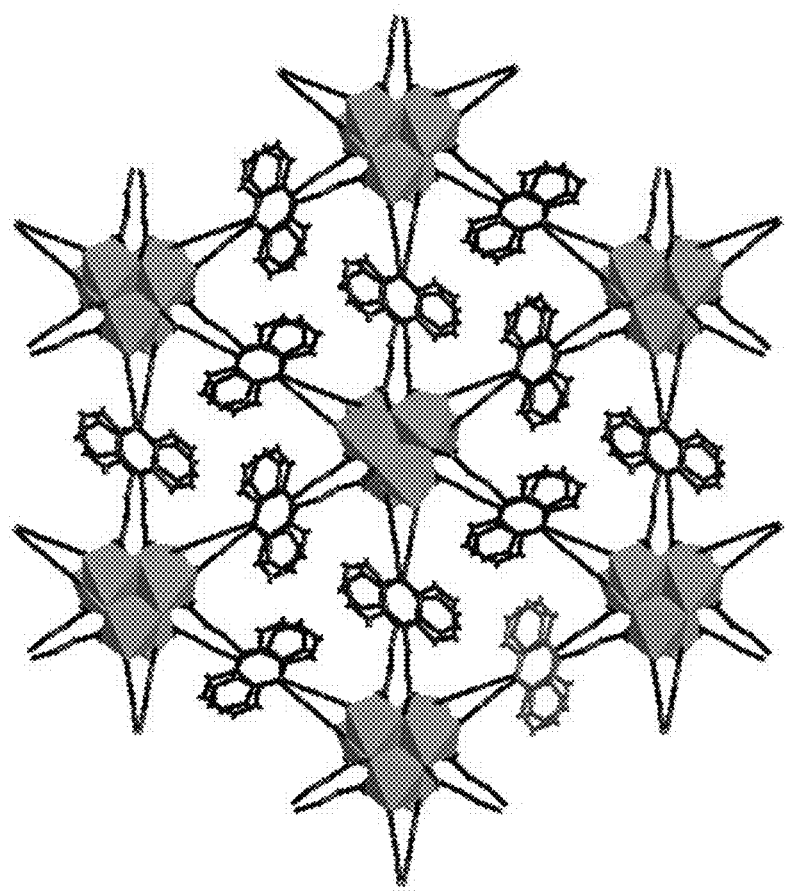
FIG. 1 shows a three dimensional structural schematic diagram of the $CO_2$ quantitative fluorescent sensing material provided in embodiments of the present disclosure.

By crystal structure analysis, the $CO_2$ quantitative fluorescent sensing material crystallizes in a trigonal $R_3$ space group. Preferably, the $CO_2$ quantitative fluorescent sensing material has a molecular formula of $C_{60}H_{36}Mn_3O_{13}$. It includes a plurality of fundamental asymmetric units. The fundamental asymmetric unit includes two L ligands, two $Mn^{2+}$, and $\frac{2}{3}\mu$-O, and the L ligand is 9,10-diacrylate anthracene. Further, each of two carboxyl groups of the L ligand takes a motif of bidentate coordination. Each of the two carboxyl groups bridges two different $Mn^{2+}$. Each of the two different $Mn^{2+}$ is hexa-coordinated. Each of the two different $Mn^{2+}$ coordinates with one $\mu$-O and five oxygen atoms of five carboxyl groups of five different L ligands, forming an octahedral geometry. Each of the $\mu$-O coordinates with three different $Mn^{2+}$, forming a $(Mn_3O)(COO)_3$ secondary building unit arranged in a way of . . . ABAB . . . in parallel along a "c" axis. Different $(Mn_3O)(COO)_3$ secondary building units connect with each other by bidentate bridging of the carboxyl group, forming a unidimensional metal chain along the "c" axis. Each of the L ligands connects with two different $(Mn_3O)(COO)_3$ secondary building units by carboxyl groups of the L ligands respectively, stacked in the way of . . . ABAB . . . along the "c" axis. Each of the different $(Mn_3O)(COO)_3$ secondary building units further connects with three of the different L ligands respectively, forming a three dimensional infinite network, as shown in FIG. 1.

The embodiments of the present disclosure also provide an application of a fluorescent sensing material for $CO_2$ quantification. The $CO_2$ quantitative fluorescent sensing, material detects a concentration of $CO_2$ quantitatively as a fluorescence detection material. An ionic liquid produced by a reaction of $CO_2$ with the amine compound, is mainly used to stimulate an aggregation-induced emission of the fluorescent sensing material for $CO_2$ quantification. The fluorescence of the $CO_2$ quantitative fluorescent sensing material is significantly enhanced so that a concentration of $CO_2$ is rapidly and accurately quantified by the fluorescence detection, The specific method for fluorescence detection of $CO_2$ concentration using the $CO_2$ quantitative fluorescent sensing material includes steps as follows.

Step 1: obtaining standard fluorescence emission spectra: a plurality of standard fluorescence emission spectra are respectively obtained by measuring the amine dispersion of $CO_2$ quantitative fluorescent sensing material after the introduction of a plurality of mixed gases of $CO_2$ and $N_2$ containing various concentrations of $CO_2$ to the amine dispersion. A concentration of $CO_2$ is marked as x, and a fluorescent intensity of a maximum emission peak is marked as y corresponding to the concentration of $CO_2$ in each of the standard fluorescence emission spectra. A standard curve with a linear relation is graphed by at least 10 groups of x, y values. A linear relationship is obtained between the concentration of $CO_2$ and the fluorescent intensity of the maximum emission peak of the standard fluorescence emission spectrum of the $CO_2$ quantitative fluorescent sensing material with a mixed gas containing $CO_2$ gas.

Wherein, the method for obtaining the standard fluorescence emission spectrum by measuring the amine dispersion of the $CO_2$ quantitative fluorescent sensing material after each introduction of the mixed gases of $CO_2/N_2$ containing various concentrations of $CO_2$ to the amine dispersion includes steps as follows.

1 mg of the $CO_2$ quantitative fluorescent sensing material is weighed and the $CO_2$ quantitative fluorescent sensing material is added into a quartz cuvette. 1 mL of an amine compound is added into the quartz cuvette, 20-30 mL of a mixed gas of $CO_2$ and $N_2$ containing a certain concentration of $CO_2$, is introduced. The quartz cuvette is immediately sealed after the introduction of the mixed gas, a reference dispersion is obtained for the mixed gas of $CO_2$ and N2 containing a certain concentration of $CO_2$. The amine compound is di-n-propylamine, di-n-butylamine, di-n-hexylamine, propylamine, diethylamine, diisopropylamine, n-butylamine, diisobutylamine, N-methylpiperazine, or N, N'-dimethylethylenediamine. Preferably, the amine compound is di-n-propylamine, di-n-butylamine or di-n-hexylamine and the effect is relatively excellent. The fluorescence emission spectrum of the reference dispersion is recorded in a wavelength range of 425-750 nm. A fluorescence spectrophotometer is used for obtaining the fluorescence spectrum; an excitation wavelength of 402 mn is set. And a standard fluorescence emission spectrum is obtained correspondent to the certain amount of $CO_2$.

Step 2: a concentration of $CO_2$ in a gas to be tested is detected. A fluorescence emission spectrum is obtained by measuring the amine dispersion of $CO_2$ quantitative fluorescent sensing material after the introduction of a mixed gas containing an unknown concentration of $CO_2$ in the gas to be tested, and an maximum emission peak is marked as y'. The concentration of $CO_2$ in the gas to be tested is calculated to be x', according to the linear relationship.

Wherein, the method for measuring a fluorescence emission spectrum of the amine dispersion of the $CO_2$ quantitative fluorescent sensing material for a gas to be tested containing an unknown concentration of $CO_2$ includes the following steps.

1 mg of the $CO_2$ quantitative fluorescent sensing material is weighed, and the $CO_2$ quantitative fluorescent sensing material is added into a quartz cuvette. 1 mL of the amine compound is added, then the gas to be tested containing the unknown concentration of $CO_2$ is introduced with a same amount of the mixed gas mentioned above. A flow rate of the gas to be tested is controlled with a same flow rate of the mixed gas mentioned above, that is, the flow rate of the gas to be tested is maintained at 10 mL/min. The quartz cuvette is immediately sealed after introducing the gas to be tested containing the unknown concentration of $CO_2$, and a dispersion to be tested is obtained.

A florescence emission spectrum of the dispersion to be tested is recorded in a wavelength range of 425-750 nm. A fluorescence spectrophotometer is used for obtaining the fluorescence spectrum; an excitation wavelength of 402 nm is set.

The principle of fluorescence detection of $CO_2$ using the $CO_2$ quantitative fluorescent sensing material is as follows.

Figure 2:
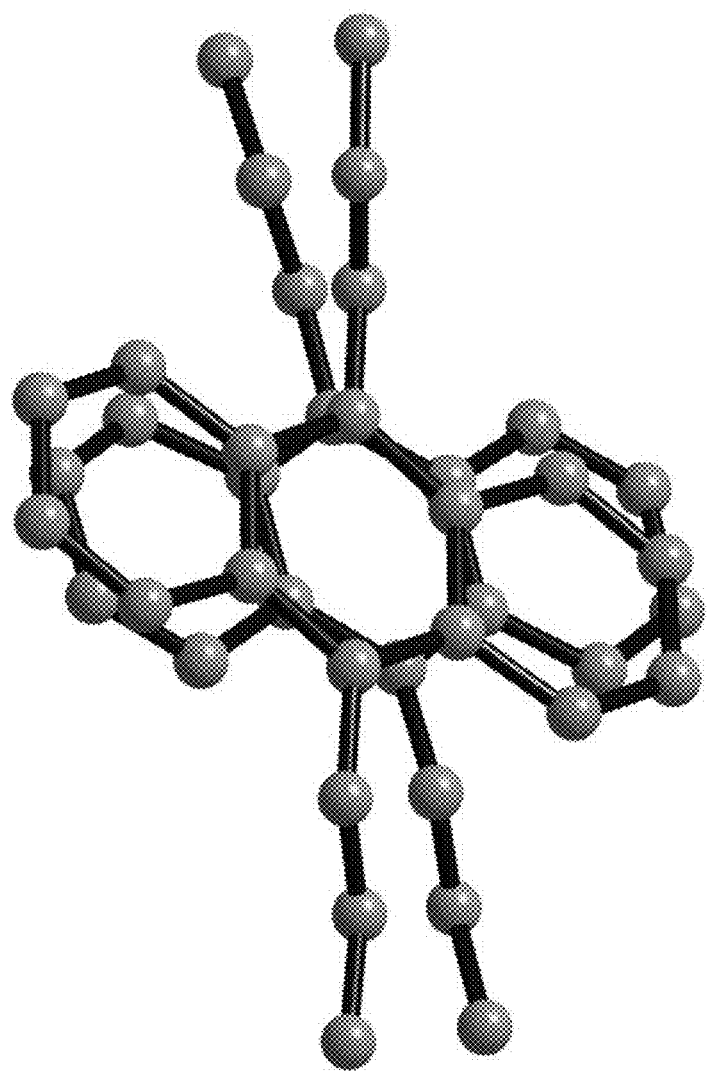
FIG. 2 shows a structural diagram of a spatial arrangement of ligands of the $CO_2$ quantitative fluorescent sensing material provided in embodiments of the present disclosure.

Above all, the fluorescent detection material used in the embodiment of the present disclosure is a fluorescent sensing material named ADA-Mn for $CO_2$ quantification, which is a three dimensional framework formed by self-assembly of 9,10-anthracene anthracene $H_2ADA$ and $Mn^{2+}$ ions. Each of two ligands pairs up, showing a periodic arrangement mode of ABAB-type, as shown in FIG. 2. This arrangement mode makes the anthracene ring of each ligand present a non-planar twisted structure. A dihedral angel of the twisted anthracene ring is about 3.221°. The twisted non-planar structure destroys an original $\pi$-conjugated system, resulting in a fluorescence quenching of the $CO_2$ quantitative fluorescent sensing material ADA-Mn under normal conditions.

Secondly, $CO_2$ rapidly and quantitatively reacts with some amines at a normal temperature and pressure to yield an ionic liquid correspondingly. The influence of the amine compounds on fluorescence properties of a sensing material before and after reacting with $CO_2$ is exploited in order to develop a fluorescence sensing method for $CO_2$ quantification. In general, a relative rotation or twist of intramolecular groups affects an electronic structure of a molecule itself. A Restricted Intramolecular Rotation (RIR) affects a way and an extent of an interaction, between molecules, so that a macroscopic fluorescence property of the molecule changes significantly to achieve an aggregation-induced emission, namely the AIE effect. In general, realization of RIR depends on a viscosity and a polarity of a solvent environment in which the fluorescent molecules are dissolved. An adjustable AIE effect can be achieved by regulating the viscosity and the polarity of the solvent in which the fluorescent molecules are, so as to realize fluorescence recognition. The present disclosure takes specifically an advantage that $CO_2$ reacts with a certain amine compound rapidly and quantitatively at normal temperature and pressure to yield an ionic liquid with high viscosity and large polarity, which restricts the twist of the anthracene ring and force the anthracene ring to restore a planar structure. So that a strong fluorescence property is shown. A significant difference in viscosity and polarity between the amine and the ionic liquid yielded by reacting the amine with $CO_2$ triggers the AIE effect of ADA-Mn based on the RIR principle, so that the fluorescence emission of ADA-Mn is greatly enhanced.

Additionally, an intensity of this fluorescence emission is linearly related to the viscosity of the ionic liquid in which the $CO_2$ quantitative fluorescent sensing material ADA-Mn is dispersed, and the viscosity of the ionic liquid depends on a concentration of $CO_2$ that is absorbed to react with the amine compound, ie, the ATE fluorescence intensity of ADA-Mn is proportional to the concentration of $CO_2$ in the gas to be detected, ie, these two parameters are linearly related.

By measuring and plotting the standard curve in advance, a determination of $CO_2$ concentration in unknown samples can be achieved quickly and accurately. The above principle depends on a characteristic reaction of $CO_2$ and the amine compound, and a response speed is quite fast. A detection of concentration range is wide (0-1.00%), In the meanwhile, there is no theoretical possibility of CO interfering with this reaction, which has been proved by a verification test. The interference of water is also negligible, a bicarbonate ionic liquid is yielded when water is involved in the reaction of $CO_2$ with an amine compound, and the bicarbonate ionic liquid has almost the same viscosity and polarity. Same results are obtained when humidified $CO_2$ is used instead of dry $CO_2$. Therefore, the fluorescence detection of $CO_2$ by the $CO_2$ quantitative fluorescent sensing material is a new fluorescence sensing technology for $CO_2$ quantification.

The features and performances of the present disclosure are further described in detail below with reference to the embodiments.

Embodiment 1

The embodiment 1 provides a fluorescent sensing material for $CO_2$ quantification, prepared according to steps below.

50 mg of 9,10-diacrylic anthracene was dissolved in 10 mL of N,N-dimethylformamide to obtain a first solution of 5 mg/mL. 500 mg of $MnCl_2$ was dissloved in 10 mL water to obtain a second solution of 50 mg/mL.

8 mL of the first solution and 2 mL of the second solution were mixed. Then 7 drops of 0.3 mol/L of a diluted nitric acid was added. And a mixed solution was obtained.

The mixed solution was sealed and heated in a glass spawn bottle for 4 days. A heating temperature was 80° C. A target Product of an orange needle crystal was obtained, which is the fluorescent sensing material for $CO_2$ quantification.

The method for fluorescence detection of $CO_2$ concentration using the $CO_2$ quantitative fluorescent sensing material includes steps as follows.

(1) measuring an original fluorescence emission spectrum.

1 mg of the $CO_2$ quantitative fluorescent sensing material was weighed and the $CO_2$ quantitative fluorescent sensing material was added into a 1 cm×1 cm quartz cuvette.

1 mL of di-n-propylamine was added into the 1 cm×1 cm quartz cuvette and the dispersion was well mixed until it was homogeneous and a standard dispersion was obtained.

A Hitachi F-4600 fluorescence spectrophotometer was used with an excitation wavelength thereof set at Ex=402 nm. A fluorescence emission spectrum of the standard dispersion was recorded in a wavelength range of 425-750 nm, obtaining a maximum emission peak at wavelength of 536 nm, and a fluorescent intensity is 57.

(2) obtaining a standard fluorescence emission spectrum by measuring the $CO_2$ quantitative fluorescent sensing material with a mixed gas of $CO_2/N_2$ containing 10% $CO_2$.

1 mg of the $CO_2$ quantitative fluorescent sensing material was weighed and the $CO_2$ quantitative fluorescent sensing material was added into a 1 cm×1 cm quartz cuvette. 1 mL of di-n-propylamine was added into the 1 cm×1 cm quartz cuvette, 20 mL of the mixed gas of $CO_2/N_2$ containing 10% $CO_2$ was introduced. A flow rate of the mixed gas was maintained at 10 mL/min. The 1 cm×1 cm quartz cuvette was immediately sealed after the introduction of the mixed gas, reference dispersion 1 was obtained.

A Hitachi F-4600 fluorescence spectrophotometer was used with an excitation wavelength thereof set at Ex=402 nm. A fluorescence emission spectrum of the standard solution was recorded in a wavelength range of 425-750 nm, obtaining a maximum emission peak at wavelength shifted to 510 nm, and a fluorescent intensity is 524.

(3) obtaining respectively standard fluorescence emission spectra by measuring the di-n-propylamine dispersion of the $CO_2$ quantitative fluorescent sensing material after an introduction of mixed gases of $CO_2/N_2$ respectively containing 10%-100% $CO_2$ to the di-n-propylamine dispersion.

Figure 3:
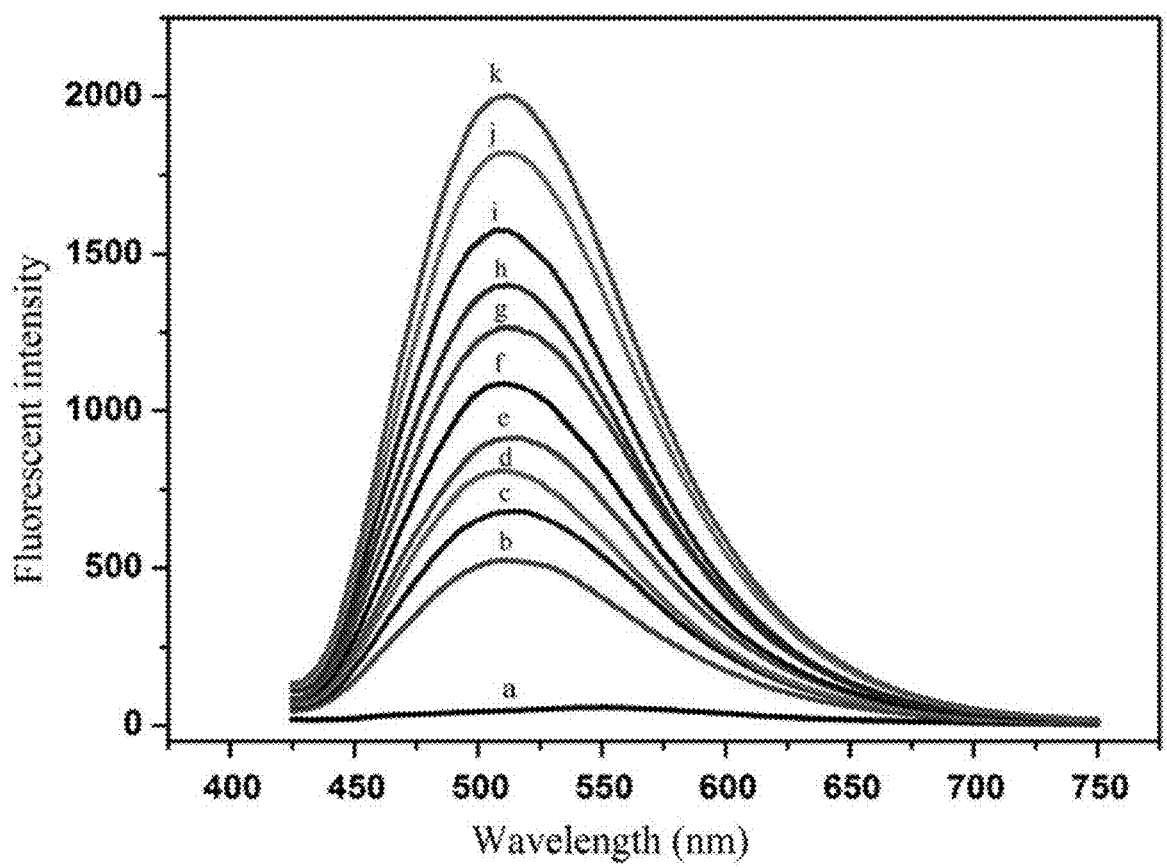
FIG. 3 shows a plurality of fluorescence emission spectra of the $CO_2$ quantitative fluorescent sensing material for a plurality of mixed gases containing various concentrations of $CO_2$ provided in embodiment 1 of the present disclosure.

According to a same method mentioned above, a mixed gas containing 20%, 30%, 40%, 50%, 60%, 70%, 80%, 90%, 100% $CO_2$ was introduced separately and respectively. Reference dispersion 2, reference dispersion 3, reference dispersion 4, reference dispersion 5, reference dispersion 6, reference dispersion 7, reference dispersion 8, reference dispersion 9, and reference dispersion 10 were respectively obtained. A fluorescence emission spectra of the reference dispersions are separately and respectively measured, as shown in FIG. 3. Line a is the fluorescence emission spectrum by measuring the di-n-propylamine dispersion of the fluorescent sensing material after introduction of a mixed gas of $CO_2/N_2$ containing 0% $CO_2$ to the di-n-propylamine dispersion; line b is the fluorescence emission spectrum by measuring the di-n-propylamine dispersion of the fluorescent sensing material alter introduction of a mixed gas of $CO_2/N_2$ containing 10% $CO_2$; line c is the fluorescence emission spectrum by measuring the di-n-propylamine dispersion of the fluorescent sensing material after introduction of a mixed gas of $CO_2/N_2$ containing 20% $CO_2$; line d is the fluorescence emission spectrum by measuring the di-n-propylamine dispersion of the fluorescent sensing material after introduction of a mixed gas of $CO_2/N_2$ containing 30% $CO_2$; line e is the fluorescence emission spectrum by measuring the di-n-propylamine dispersion of the fluorescent sensing material after introduction of a mixed gas of $CO_2/N_2$ containing 40% $CO_2$; line f is the fluorescence emission spectrum by measuring the di-n-propylamine dispersion of the fluorescent sensing material after introduction of a mixed gas of $CO_2/N_2$ containing 50% $CO_2$; line g is the fluorescence emission spectrum by measuring the di-n-propylamine dispersion of the fluorescent sensing material after introduction of a mixed gas of $CO_2/N_2$ containing 60% CO2; line h is the fluorescence emission spectrum by measuring the di-n-propylamine dispersion of the fluorescent sensing material after introduction of a mixed gas of $CO_{21}/N_2$ containing 70% $CO_2$; line i is the fluorescence emission spectrum by measuring the di-n-propylamine dispersion of the fluorescent sensing material after introduction of a mixed gas of $CO_2/N_2$ containing 80% $CO_2$; line j is the fluorescence emission spectrum by measuring the di-n-propylamine dispersion of the fluorescent sensing material after introduction of a mixed gas of $CO_2/N_2$ containing 90% $CO_2$; line k is the fluorescence emission spectrum by measuring the di-n-propylamine dispersion of the fluorescent sensing material after introduction of a mixed gas of $CO_2/N_2$ containing 100% $CO_2$.

A $CO_2$ concentration is marked as x, and a correspondent fluorescent intensity of the maximum emission peak of a fluorescence spectrum is marked as y. Results of x, y are shown below.

| Objective of measurement | Concentration of $CO_2$/x | Fluorescent intensity/y |
| --- | --- | --- |
| Standard dispersion | 0 | 57 |
| Reference dispersion 1 | 10% | 524 |
| Reference dispersion 2 | 20% | 683 |
| Reference dispersion 3 | 30% | 810 |
| Reference dispersion 4 | 40% | 913 |
| Reference dispersion 5 | 50% | 1089 |
| Reference dispersion 6 | 60% | 1267 |
| Reference dispersion 7 | 70% | 1402 |
| Reference dispersion 8 | 80% | 1576 |
| Reference dispersion 9 | 90% | 1823 |
| Reference dispersion 10 | 100% | 2002 |

Figure 4:
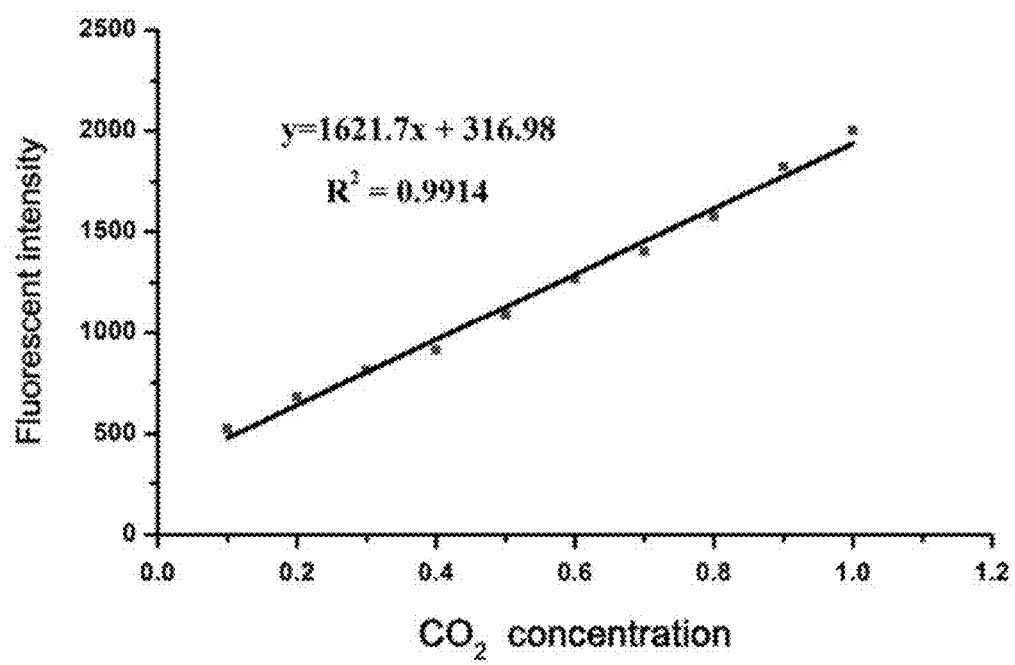
FIG. 4 shows a standard curve with a linear relationship between a fluorescent intensity of an amine dispersion of the $CO_2$ quantitative fluorescent sensing material after introduction of a gas containing $CO_2$ and a concentration of $CO_2$ provided in embodiment 1 of the present disclosure.

According to the ten groups of x values (10%-100%) in the above table, a standard linear regression line is graphed between the concentration of $CO_2$ x and the fluorescent intensity y based on data of x, y values written above, shown as FIG. 4. As seen in FIG. 4, a linear relationship between the fluorescent intensity value y of the $CO_2$ quantitative fluorescent sensing material with a $CO_2$ concentration value x in a gas containing $CO_2$: $y=1621.2x+316.98$.

(4) measuring the fluorescence emission spectrum of the amine dispersion of the $CO_2$ quantitative fluorescent sensing material for the gas to be tested containing an unknown concentration of $CO_2$.

1 mg of the $CO_2$ quantitative fluorescent sensing material was weighed, and the $CO_2$ quantitative fluorescent sensing material was added into a 1 cm×1 cm quartz cuvette. 1 mL of the same amine compound was added as mentioned above, then the gas to be tested containing the unknown concentration of $CO_2$ was introduced with a same amount of the mixed gas mentioned above. A flow rate of the gas to be tested containing the unknown concentration of $CO_2$ was controlled with a same introducing speed of the mixed gas, that is, the flow rate was maintained at 10 mL/min. The 1 cm×1 cm quartz cuvette was immediately sealed after introduction of the gas to be tested containing the unknown concentration of $CO_2$, and a dispersion to be tested was obtained;

The dispersion to be tested was measured at a wavelength range of 425-750 nm and a florescence emission spectrum was obtained. A fluorescence spectrophotometer was used for detecting the fluorescence spectrum. An excitation wavelength of 402 nm was set. The fluorescence emission spectrum was obtained and a fluorescent intensity of the maximum emission peak was 902. According to the linear relationship $y=1621.7x+316.98$, a concentration of $CO_2$ in the gas to be tested was calculated to be 36%.

Embodiment 2

Embodiment 2 provides a fluorescent sensing material for $CO_2$ quantification, prepared by the following steps.

100 mg of 9,10-diacrylic anthracene was dissolved in 10 mL of N,N-dimethylacetamide to obtain a first solution of 10 mg/mL. 1 g of $MnCl_2$ was dissloved in 10 mL of water to obtain a second solution of 100 mg/mL.

2 mL of the first solution and 8 mL of the second solution were mixed. Then 3 drops of 1 mol/L of a diluted hydrochloric acid was added. And a mixed solution was obtained.

The mixed solution was sealed and heated in a glass spawn bottle for 2 days. A heating temperature was 90° C. A target product of an orange needle crystal was obtained, which is the fluorescent sensing material for $CO_2$ quantification.

Embodiment 3

Embodiment 3 provides a fluorescent sensing material for $CO_2$ quantification, prepared by the following steps.

80 mg of 9,10-diacrylic anthracene was dissolved in 10 mL of N,N-diethylformamide to obtain a first solution of 8 mg/mL. 800 mg of $MnCl_2$ was dissloved in 10 mL of water to obtain a second solution of 80 mg/mL.

5 mL of the first solution and 5 mL of the second solution were mixed. Then 5 drops of 0.7 mol/L of a diluted nitric acid was added. And a mixed solution was obtained.

The mixed solution was sealed and heated, in a glass spawn bottle for 6 days. A heating temperature was 70° C. A target product of an orange needle crystal was obtained, which is the fluorescent sensing material for $CO_2$ quantification.

The embodiments of the present disclosure also provides an application of a fluorescent sensing material for $CO_2$ quantification. The $CO_2$ quantitative fluorescent sensing material detects a concentration of $CO_2$ quantitatively as a fluorescence detection material. An ionic liquid produced by a reaction of $CO_2$ with the amine compound, is mainly used to stimulate an aggregation-induced emission of the fluorescent sensing material for $CO_2$ quantification. The fluorescence of the $CO_2$ quantitative fluorescent sensing material is significantly enhanced so that a concentration of $CO_2$ is rapidly and accurately quantified by the fluorescence detection.

The embodiments are only a part but not all of the embodiments of the present disclosure. The detailed description of the embodiments of the disclosure is not intended to limit a protection scope of the disclosure, but merely to present selected embodiments of the disclosure. All other embodiments obtained by those skilled in the art based on the embodiments of the present disclosure without creative efforts shall fall within a protection scope of the present disclosure.

What is claimed is:

1. A preparation method of a $CO_2$ quantitative fluorescent sensing material, characterized in that the method comprises:
dissolving 9.10-diacrylic anthracene in a solvent and obtaining a first solution of 5-10 mg/mL;
the solvent is any one of N,N-dimethylformamide, N,N-dimethylacetamide and N,N-diethylformamide;
dissolving $MnCl_2$ or $Mn(ClO_4)_2$ in water and obtaining a second solution of 50-100 mg/mL;
mixing the first solution and the second solution in a volume ratio of 4:1-1:4;
adding a dilated acid with a $H^+$concentration of 0.3-1 mol/L and obtaining a mixed solution; and
sealing and heating the mixed solution for 2-6 days under a heating temperature at 70-90° C.

2. The preparation method of the $CO_2$ quantitative fluorescent sensing material according to claim 1, characterized in that the diluted acid is a diluted nitric acid or a diluted hydrochloric acid.

3. The preparation method of the $CO_2$ quantitative fluorescent sensing material according to claim 1, characterized in that the mixed solution is sealed and heated in a glass spawn bottle.

4. A $CO_2$ quantitative fluorescent sensing material, characterized in that the fluorescent sensing material is prepared by the method of claim 1.

5. A method of performing a fluorescent $CO_2$ quantification using the $CO_2$ quantitative fluorescent sensing material according to claim 4, characterized in that the $CO_2$ quantitative fluorescent sensing material is used as a fluorescent detection material, and the method comprises:
obtaining standard fluorescence emission spectra by measuring an amine dispersion of the $CO_2$ quantitative fluorescent sensing material after an introduction of mixed gases of $CO_2$ and $N_2$ containing various concentrations of $CO_2$ respectively to the amine dispersion;
marking a concentration of $CO_2$ as x, and marking corresponding fluorescent intensity of a maximum emission peak of the standard fluorescent spectra as y;
graphing a standard curve with a linear relationship by at least 10 groups of x, y values;
obtaining the linear relationship between the concentrations of $CO_2$ and the fluorescent intensity of the maximum emission peak of the standard fluorescence emission spectra of the $CO_2$ quantitative fluorescent sensing material with the mixed gases containing various concentrations of $CO_2$,
recording a fluorescence emission spectrum of an amine dispersion of the $CO_2$ quantitative fluorescent sensing material, after introduction of a mixed gas containing an, unknown concentration of $CO_2$, and marking a maximum emission peak as y'; and
calculating a concentration of $CO_2$ to be x' in the gas to be tested according to the linear relationship.

6. The method according to claim 5, characterized in that a method for obtaining the standard fluorescence spectrum by measuring the amine dispersion of the $CO_2$ quantitative fluorescent sensing material after each introduction of the mixed gases of $CO_2$ and $N_2$ containing various concentrations of $CO_2$ to the amine dispersion comprises:
weighing 1 mg of the $CO_2$ quantitative fluorescent sensing material and adding the $CO_2$ quantitative fluorescent sensing material into a quartz cuvette;
adding 1 mL of an amine compound into the quartz cuvette, and introducing 20-30 mL of the mixed gas of $CO_2$ and $N_2$ containing a certain concentration of $CO_2$;
sealing the quartz cuvette immediately after introducing the mixed gas, and obtaining a reference dispersion;
recording the fluorescence emission of the reference dispersion in a wavelength range of 425-700 nm; and
obtaining the standard fluorescence spectrum corresponding to the certain concentration of $CO_2$.

7. The method according to claim 6, characterized in that a method for measuring the fluorescence spectrum of the $CO_2$ quantitative fluorescent sensing material for the gas to be tested containing an unknown concentration of $CO_2$ comprises:
weighing 1 mg of the fluorescent sensing material for $CO_2$ quantification, and adding the $CO_2$ quantitative fluorescent sensing material into a quartz cuvette;
adding 1 mL of the amine compound, then introducing the gas to be tested containing the unknown concentration of $CO_2$ with an amount of the mixed gas same to the corresponding standard fluorescence spectrum test;
controlling a flow rate of the gas to be tested containing the unknown concentration of $CO_2$ with a flow rate of the mixed gas same to the corresponding standard fluorescence spectrum test;
sealing the quartz cuvette immediately after introducing, the gas to be tested containing the unknown concentration of $CO_2$, and obtaining a dispersion to be tested;
recording a fluorescence emission of the dispersion of the $CO_2$ quantitative fluorescent sensing material in a wavelength range of 425-750 nm; and
obtaining a fluorescence emission spectrum.

8. The method according to claim 6, characterized in that a fluorescence spectrophotometer is used for recording the fluorescence emission spectrum; and an excitation wavelength is set to be 402 nm before use.

9. The method according to claim 6, characterized in that the amine compound is di-n-propylamine, di-n-butylamine, di-n-hexylamine, propylamine, diethylamine, diisopropylamine, n-butylamine, diisobutylamine, N-methylpiperazine, or N,N'-dimethylethylenediamine.

* * * * *